United States Patent [19]
Albers et al.

[11] Patent Number: 4,691,069
[45] Date of Patent: Sep. 1, 1987

[54] HYDROGENTATION OF UNSATURATED ALIPHATIC HYDROCARBONS

[75] Inventors: Michel O. Albers; Eric Singleton, both of Pretoria, South Africa

[73] Assignee: South African Inventions Development Corporation, Pretoria, South Africa

[21] Appl. No.: 831,006

[22] Filed: Feb. 19, 1986

[30] Foreign Application Priority Data

Feb. 26, 1985 [ZA] South Africa ................... 85/1445

[51] Int. Cl.$^4$ .............................................. C07C 5/03
[52] U.S. Cl. ................................. 585/259; 585/273
[58] Field of Search ............................. 585/259, 273

[56] References Cited

U.S. PATENT DOCUMENTS 3,454,644 7/1969 Dewhirst ........................... 585/273

FOREIGN PATENT DOCUMENTS 1141847 2/1969 United Kingdom .

OTHER PUBLICATIONS

Lapporte et al., J. Org. Chem., 28, Jul. 1963, pp. 1947–1948.
R. Pearce & W. R. Patterson, Catalysis and Chemical Processes, Blackie, Glasgow 1981, 305.
S. Slater & EL. L. Muetterties, Inorg. Chemistry (1980), 19,3337–3342.
L. S. Stuhl & E. L. Muetterties, Ingorg. Chemistry (1979), 17,2148.
C. U. Pitman, R. C. Ryan, J. McGee & J. P. O'Connor-J. Organomet Chemistry 1978(1979) C43.
R. R. Schrock & J. A. Osborn, J. Am. Chem. Soc.-98(1976)2134.
R. H. Crabtree, A. Gautier, G. Giordano & T. Kahn-J. Organomet. Chem. 141(1977) 113.
Chemical Abstract (1969), vol. 71, 83317.

Primary Examiner—Curtis R. Davis
Attorney, Agent, or Firm—Ladas & Parry

[57] ABSTRACT

The invention provides a process for the catalytic hydrogenation of an unsaturated hydrocarbon, particularly useful for the hydrogenation of alkynes such as acetylene to alkenes such as ethylene. The unsaturated hydrocarbon is brought into contact with hydrogen in the presence of a catalyst which comprises cations selected from the group consisting in five-coordinate and six-coordinate complex cations of ruthenium (II) having the general formula (1):

$$(RuXL_n)^+ \qquad (1)$$

in which:
  X is a radical;
  L is a donor ligand; and
  n is an integer not greater than 5.

26 Claims, 8 Drawing Figures

- ● — ACETONE
- ☐ — ACETONE: METHANOL  4:1
- ○ —     "           "    3:1
- △ —     "           "    1:1
- ▲ —     "           "    1:3

● - CONTROL
○ - 1.0 MOLAR EQUIVALENTS
△ - 2.5 " "
▲ - 5 and 10 " "

HYDROGENTATION OF UNSATURATED ALIPHATIC HYDROCARBONS

This invention relates to a process for the hydrogenation of an unsaturated aliphatic hydrocarbon. More particularly the invention relates to a process suitable for the hydrogenation of alkynes to alkenes.

According to the invention there is provided a process for the hydrogenation of an unsaturated aliphatic hydrocarbon which comprises bringing an unsaturated aliphatic hydrocarbon to be hydrogenated into contact with hydrogen in the presence of a catalyst which comprises cations selected from the group consisting in five-coordinate and six-coordinate complex cations of ruthenium (II) having the general formula (1):

$$(RuXL_n)^+ \quad (1)$$

in which:
X is a radical;
L is a donor ligand; and
n is an integer not greater than 5.

These cations are obtainable from precursor complexes of ruthenium (II) having the general formula (2):

$$(RuXL_n)Y \quad (2)$$

in which X and L are as defined above and Y is a suitable anionic counterion.

The radical may be a radical selected from the group comprising H, halogens such as Br and Cl, $SO_4$, $NO_3$, $RSO_3$ and $RCOO$ in which R is H or a hydrocarbon radical.

There may be more than one donor ligand which may be the same or different and may be monodentate or polydentate, e.g. bidentate, and the dentation thereof will be selected, together with the value of n, so that the cations of formula (1) are either five-coordinate or six-coordinate. At least one donor ligand may be a ligand selected from monodentate and bidentate ligands, the cation containing e.g. four or five monodentate ligands, two bidentate ligands and a monodentate ligand or a bidentate ligand and two or three monodentate ligands. In principle the cation can contain a ligand with a dentation higher than two, provided that any other ligands in the cation have a dentation such that the cation is five-coordinate or six-coordinate.

At least one ligand may be an organic molecule containing at least one atom therein which has a lone pair of electrons, said atom being selected from P, As, Sb and Bi, and having a suitable valency state typically a valency state of three, which provides said lone pair of electrons.

At least one ligand L may be a tertiary organic compound in accordance with the formula:

$$R^1R^2R^3E \quad (3)$$

in which
E is an atom of P, As, Sb or Bi; and
$R^1$, $R^2$ and $R^3$ are the same or different radicals and are hydrogen, alkyl, aryl, aralkyl, alkaryl, substituted alkyl, substituted aryl, substituted aralkyl or substituted alkaryl, the substituents in $R^1$, $R^2$ and $R^3$ being selected from alkyl, aryl, aralkyl, alkaryl, aryloxy, alkoxy, hydroxy, halogeno, amino, amido and nitro groups.

Instead or in addition, at least one ligand L may be a tertiary organic compound in accordance with the formula:

$$(R^1O)(R^2O)(R^3O)E \quad (4)$$

in which
E is an atom of P, As, Sb or Bi; and
$R^1$, $R^2$ and $R^3$ are the same or different radicals and are hydrogen, alkyl, aryl, aralkyl, alkaryl, substituted alkyl, substituted aryl, substituted aralkyl or substituted alkaryl, the substituents in $R^1$, $R^2$ and $R^3$ being selected from alkyl, aryl, aralkyl, alkaryl, aryloxy, alkoxy, hydroxy, halogeno, amino, amido and nitro groups.

Instead or in addition, at least one ligand L may be a tertiary organic compound in accordance with the formula:

$$R^1R^2ER^3E\,R^4R^5 \quad (5)$$

in which
E is an atom of P, As, Sb or Bi;
$R^1$, $R^2$, $R^4$ and $R^5$ are the same or different and are hydrogen, alkyl, aryl, aralkyl, alkaryl, substituted alkyl, substituted aryl, substituted aralkyl or substituted alkaryl; and $R^3$ is substituted or unsubstituted alkyl, aryl, aralkyl or alkaryl, the substituents in $R^1$, $R^2$, $R^3$, $R^4$ and $R^5$ being selected from alkyl, aryl, aral aralkyl, alkaryl, aryloxy, alkoxy, hydroxy, halogeno, amino, amido and nitro groups, and $R^3$ being bonded to both of the E atoms.

Instead or in addition, at least one ligand L may be a tertiary organic compound in accordance with the formula:

$$(R^1O)(R^2O)ER^3E(OR^4)(OR^5) \quad (6)$$

in which
E is an atom of P, As, Sb or Bi;
$R^1$, $R^2$, $R^4$ and $R^5$ are the same or different and are hydrogen, alkyl, aryl, aralkyl, alkaryl, substituted alkyl, substituted aryl, substituted aralkyl or substituted alkaryl; and $R^3$ is substituted or unsubstituted alkyl, aryl, aralkyl or alkaryl, the substituents in $R^1$, $R^2$, $R^3$, $R^4$ and $R^5$ being selected from alkyl, aryl, aralkyl, alkaryl, aryloxy, alkoxy, hydroxy, halogeno, amino, amido and nitro groups, and $R^3$ being bonded to both of the E atoms.

Particular examples of ligands which can be employed are bis(diphenylphosphino)butane, bis(diphenylphosphino)propane, $PMe_3$, $PMe_2Ph$, $P(OMe)_2Ph$, $PMe_2(C_6H_4OMe\text{-}o)$ and $AsMe_3$ in which Me is methyl and Ph is phenyl.

It should also be noted that the possibility is contemplated that one of the ligands can be coordinated also to the Ru atom to provide the X radical.

In the formula (2) above for the precursor complex, the anionic counterion Y may be a halide, hexafluorophosphate, tetraphenylborate or the like suitable species. The precursor complex which $C_8H_{12}$ is may be synthesized from $((C_8H_{12})RuH(NH_2NMe_2)_3)PF_6$ (in which $C_8H_{12}$ is cycloocta-1,5-diene and Me is methyl) and the appropriate number, e.g. 4 or 5, molar equivalents of donor ligand (as described for example by Ashworth et al in *J. Chem. Soc., Chem. Commun.* (1976) 705); or it may be generated in situ in a similar manner; or generated in situ from $((C_8H_{12})RuHL_3)PF_6$ (where $C_8H_{12}$ is as defined above and L is the donor ligand) and two molar equivalents of the donor ligand; or it may be synthesized as described by Ashworth et al in *J. Chem. Soc., Dalton. Trans.*, (1977) 1816.

The hydrogenation may be carried out with the unsaturated hydrocarbon in the gas phase or in the liquid phase, by exposing the hydrocarbon to the hydrogen at a convenient temperature and pressure, in the presence of the catalyst. Generally, the higher the pressure, the faster the reaction. The unsaturated hydrocarbon to be hydrogenated may be brought into contact with a stoichiometric excess of hydrogen, with mixing if necessary. However, the possibility is contemplated that there may be situations where, depending on the ligands present, solvent used, etc, an excessive hydrogen pressure may promote the formation in the reaction mixture of complex Ru hydride cations which display a relatively reduced catalytic activity, and experimentation will be required to determine whether or not this situation exists. Although increasing temperatures speeds up the reaction rate, it should be noted however that cation catalysts according to the invention can become deactivated when certain maximum temperatures are exceeded. This deactivation reduces the rate of hydrogenation and for this reason should be avoided, although it seems to have no other adverse effects, e.g. on selectivity or the like.

The catalyst may be homogeneous, the hydrogenation being carried out with the unsaturated hydrocarbon to be hydrogenated in the liquid phase, the catalyst being dissolved in the liquid phase and the hydrogen being in the gas phase.

If desired, said unsaturated hydrocarbon may be dissolved in a solvent, e.g. a suitably chemically inert solvent, such as an organic solvent which may be a polar organic solvent, e.g. a solvent selected from alcohols, ethers and carbonyl compounds such as ketones.

In these cases, the liquid phase may comprise, dissolved in the solvent, at least 0,1% on a molar basis of said unsaturated hydrocarbon, up to a saturated solution of the unsaturated hydrocarbon in the solvent. Similarly, the liquid phase may comprise, dissolved therein, at least 0,1% on a molar basis of the catalyst, up to a saturated solution of the catalyst in the liquid phase.

The hydrogen may be present as an atmosphere over the solution, although it can be bubbled therethrough, and the solution can be agitated if desired. Ambient temperatures and pressures (20-25° C. and atmospheric pressure) can be used, although these can be varied as described above.

Instead, the catalyst may be heterogeneous, being supported on an inert support, a mixture containing said unsaturated hydrocarbon and hydrogen being passed over the supported catalyst. Thus, said unsaturated hydrocarbon and the hydrogen may both be in the gas phase.

For example, a gaseous mixture of the unsaturated hydrocarbon and hydrogen can be passed through a bed of supported catalyst, which catalyst can be supported on a porous or granular support, such as celite (diatomaceous earth); and indeed for use in liquid phase reactions, where the hydrocarbon to be saturated makes up the liquid phase by itself or dissolved in a solvent, a supported catalyst may be provided by supporting the catalyst on a cation exchange resin. Once again these reactions can, subject to possible catalyst deactivation, take place at ambient or elevated (or reduced) temperatures and pressures.

It is contemplated that, by virtue of the flexibility and ease of the reaction, that process parameters can be varied within considerable limits and the best temperatures, pressures, proportions of reagents and catalysts, reaction vessel sizes, catalyst bed sizes and geometries, residence times, flow rates, etc will be determined by routine experimentation, taking practical and economic considerations into account.

The process of the invention can be used to hydrogenate alkynes, alkenes or mixtures thereof to alkanes, or as described hereunder, for the selective hydrogenation of alkynes to alkenes.

However, although the invention can be used to hydrogenate alkynes and/or alkenes to alkanes, it is contemplated that the prime utility of the invention will be to hydrogenate alkynes to alkenes. This is because, as described hereunder, the selectivity of the process for the production of alkenes can be promoted at the expense of alkane production. The invention will accordingly be described hereunder with particular reference to the hydrogenation of alkynes to alkenes.

In accordance with the process of the present invention, deactivation of the catalyst can be resisted or retarded, particularly in the liquid phase reaction carried out with a homogeneous catalyst, by adding an excess of a suitable ligand to the catalyst solution in the unsaturated hydrocarbon, with or without the aforesaid solvent. The applicant has also found, surprisingly, that adding the excess ligand, which may be the same or different from the ligand or ligands present in the catalyst and may be a mixture of different species, promotes the formation of alkenes from alkynes at the expense of alkanes. In other words, in the hydrogenation of alkynes, selectivity for alkenes is promoted.

Thus, in a particular embodiment of the invention, said unsaturated hydrocarbon may be an alkyne, being selectively hydrogenated to an alkene, the unsaturated hydrocarbon being brought into contact with the hydrogen in the presence of said catalyst and in the presence of excess ligands. The excess ligands may be selected from ligands in accordance with at least one of formula (3), (4), (5), (6) set out above, and mixtures thereof.

The ratio on a molar basis of the excess ligands to the catalyst may be between 1:1 and 100:1, conveniently between 15:1 and 20:1.

Thus, in a particular embodiment, the alkyne may be in the liquid phase, the excess ligands being dissolved in the liquid phase, the catalyst being homogeneous and being dissolved in the liquid phase, and the ratio on a molar basis between the excess ligands and the catalyst being between 1:1 and 100:1. Preferably, the ratio is between 15:1 and 20:1.

Instead, the catalyst may be heterogeneous, being supported on an inert support, a mixture comprising said alkyne and hydrogen being passed over the supported catalyst, the mixture containing said excess ligands and the excess ligands being present in a proportion of at least 0,1% on a molar basis of the alkyne. In this case, the mixture comprising said alkyne and hydrogen may be in the gas phase.

The process of the present action is applicable to unsaturated hydrocarbons such as alkynes and alkenes where the unsaturated bonds are either internal, terminal or both internal and terminal, as with molecules having several unsaturated bonds.

The alkyne starting material which is hydrogenated may form part of a mixture comprising an alkene. In a particular embodiment, the alkyne which is hydrogenated may be acetylene, being hydrogenated to ethylene.

The Applicant has found that certain catalyst cations in accordance with formula (1) above are particularly useful for the selective hydrogenation of alkynes, which may be in the presence of alkenes, to form alkenes without hydrogenating such alkenes as are originally present or as are formed by the hydrogenation of the alkynes, to alkanes. These catalysts selectively reduce internal or terminal alkyne bonds without reducing alkene bonds, and are those in accordance with formula (1) in which the ligands L are the same or different and are one or more of PMe$_2$Ph, P(OMe)$_2$Ph, PMe$_2$(C$_6$H$_4$OMe-o) and AsMe$_3$. Of these, the ligand L which is PMe$_2$Ph shows substantial promise, and in these catalyst cations the radical X is conveniently H. These catalyst cations can conveniently be derived from precursors in accordance with formula (2) in which the anionic counterion is hexafluorophosphate, i.e. PF$_6^-$. These precursors can be obtained as described by Ashworth et al in *J. Chem. Soc. Dalton Trans.*, (1977) 1816. These cations are accordingly six-coordinate cations in accordance with formula (1) which can be represented by (RuHL$_5$)$^+$ which have five monodentate ligands L.

The Applicant has further found that certain further cations in accordance with formula (1), namely five-coordinate cations in which the radical X is hydrogen and the ligands L are the bidentate ligands bis(diphenylphosphino)propane and/or bis(diphenylphosphino)butane are useful for the hydrogenation of alkynes to alkenes and alkanes or for the hydrogenation of alkenes to alkanes. When using these catalyst cations, the Applicant has found that selection of an appropriate solvent for the catalyst and alkyne starting material promotes the selectivity of the reaction for alkenes, so that an enhanced proportion of alkenes is produced at the expense of alkanes, when an alkyne starting material is hydrogenated. Thus, for example, using a mixed acetone/methanol solvent, a higher proportion of methanol promotes alkene hydrogenation and leads to a higher proportion of the alkane in the product; and a lower proportion of methanol promotes alkyne hydrogenation and leads to a higher proportion of alkene in the product.

The invention will now be described, by way of illustrative example, with reference to the following worked Examples and accompanying drawings, in which.

EXAMPLE 1

The catalyst precursor (RuH(PMe$_2$ Ph)$_5$)PF$_6$ was prepared and purified according to the method described in Ashworth et al, *J. Chem. Soc., Dalton. Trans.*, (1977) 1816, and alkyne and alkene starting materials were purified by passage thereof through a short silica gel column, after which they were subjected to several freeze/thaw cycles under vacuum to remove air. Hexane, heptane and octane were used as non-interfering standards for gas/liquid chromatography analysis, and were de-oxygenated using freeze/thaw techniques.

In a typical experiment, $1 \times 10^{-4}$ moles of said precursor were dissolved in nitrogen degassed methanol, made up to a total volume of 50 ml and charged into a 300 ml Schlenk flask with a magnetic stirring bar. This reaction solution was frozen at $-196°$ C. and the reaction flask evacuated to $1 \times 10^{-1}$ torr.

Hydrogen was then admitted to the flask at one atmosphere pressure, and the catalyst solution was warmed to the reaction temperature in question in an oil bath provided with a thermostatic control ($\pm 0,1°$ C.). $5 \times 10^{-3}$ moles of internal standard and $1 \times 10^{-2}$ moles of the alkyne to be hydrogenated were added by syringe. The progress of the reaction was monitored at 15 minute intervals by gas/liquid chromatography analysis using a Varian series 3700 instrument available from Varian Instrument Group, Palo Alto, Calif. U.S.A. fitted with a 2,5 meter, 10% 1,2,3,-tris(2-cyanoethoxy)-propane on Chromosorb P-AW, column. The Chromosorb is available from Johns-Manville, Denver, Colo., U.S.A. The column was operated at temperatures in the range 40°–85° C. When phenylacetylene was the starting material to be hydrogenated, a 2 meter, 10% OV-101 on Chromosorb P-AW, column, operating at 85° C. was used. The OV-101 is available from Supelco Inc. U.S.A. The particular non-interfering internal standard used (hexane, heptane or octane) had no detectable influence on the results.

Figure 1:
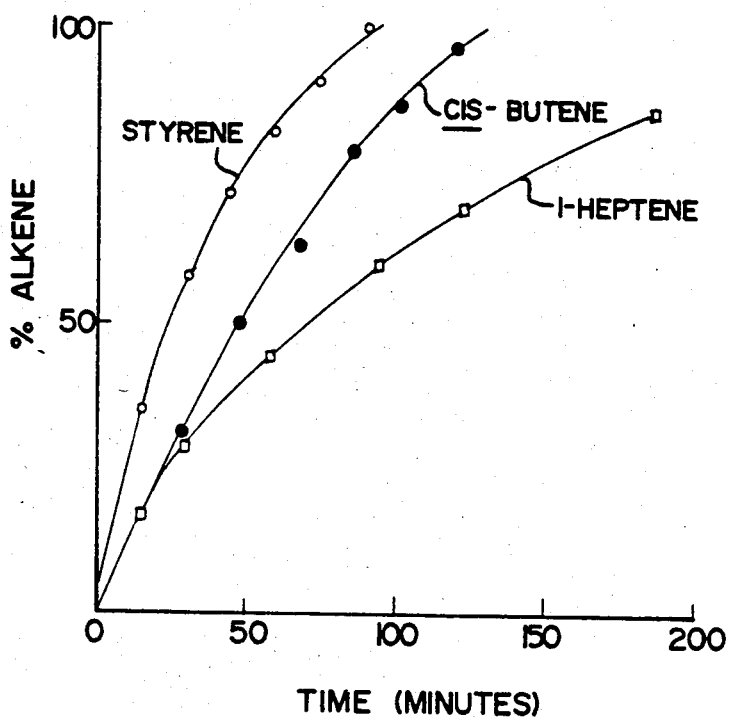
FIG. 1 is a plot against time of the proportion of alkene produced in a reaction mixture as a percentage of total theoretical alkene producible (theoretical yield) in a process in accordance with the present invention.
Figure 2:
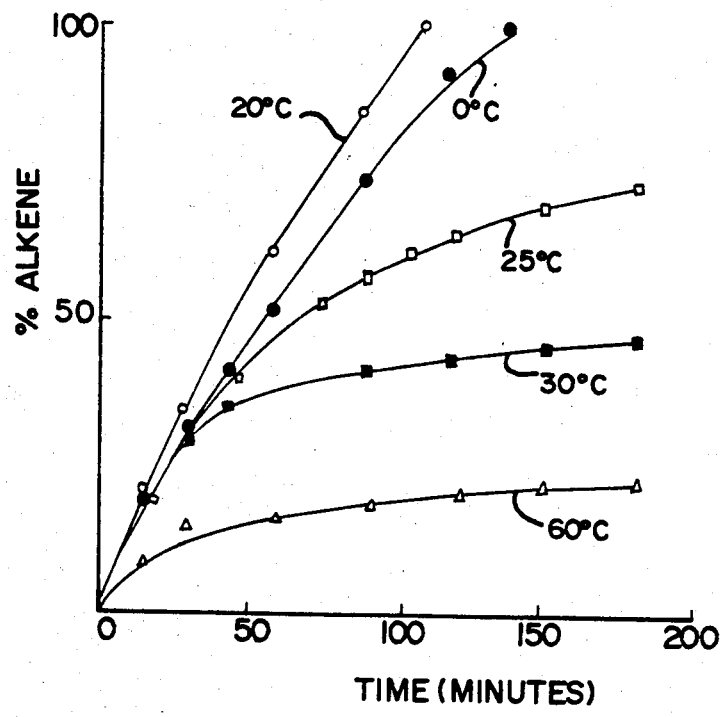
FIG. 2 is a plot against time of the proportion of alkene produced in a reaction mixture as a percentage of theoretical yield in another process in accordance with the invention.

It was found that the RuH(PMe$_2$ Ph)$_5^+$ cations derived from said precursor readily hydrogenated both terminal alkyne bonds (tested on 1-heptyne, 1-hexyne and phenylacetylene) and internal alkyne bonds (tested on 2-butyne) to the corresponding alkenes under mild reaction conditions. It was noted that the hydrogenation of 2-butyne to cis-2-butene occurred with relative ease, and that no isomerization or hydrogenation of the alkenes was observed at any stage, as tested for by the gas/liquid chromatography monitoring. It is to be emphasised that this lack of isomerization continued even after all the alkyne in question was consumed. Results are shown in FIG. 1, which is a plot of the alkene present in the reaction mixture as a percentage of the total theoretical alkene producible (theoretical yield), against time plotted respectively for 1-heptene derived from 1-heptyne and using methanol as a solvent; for cis-2- butene derived from 2-butyne with methanol as solvent, and for styrene derived from phenylacetylene using acetone as solvent, at 20° C. and with the hydrogen present at 1 atmosphere pressure. During the reaction the reaction mixture was stirred by means of the magnetic stirring bar but at a rate insufficient to entrain any of the hydrogen atmosphere in the reaction mixture. For the hydrogenation of 1-hexyne in the methanol solvent, the hydrogenation was carried out at different temperatures, namely 0° C., 20° C., 25° C., 30° C. and 60° C. to study the effect of temperature, and these results are plotted in FIG. 2 which is a plot of alkene (1-hexene) produced as a percentage of theoretical yield against time at the temperatures in question. It was found that above 20° C. more or less extensive catalyst deactivation occurred, but it was noted that this deactivation appeared only to influence the rate of alkyne hydrogenation, and a corresponding decrease in selectivity was not observed.

Figure 3:
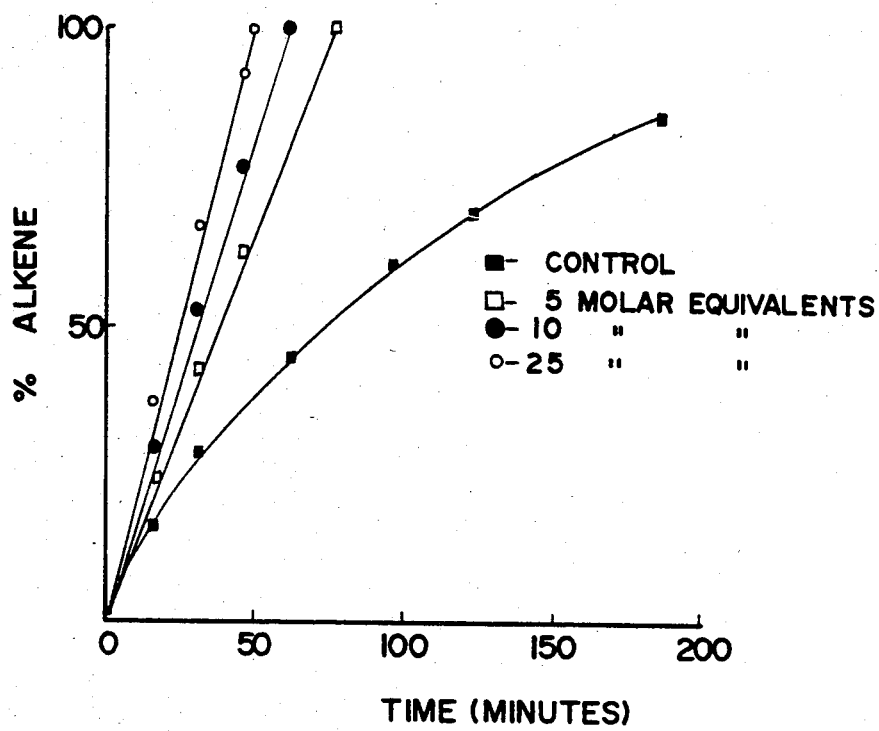
FIG. 3 is a plot against time of the proportion of alkene produced in a reaction mixture as a percentage of theoretical yield in yet another process in accordance with the invention.

It was found that this deactivation could, however, be significantly reduced by the addition of excess $PMe_2Ph$ ligand to the catalyst solution. FIG. 3 shows a plot similar to FIG. 2 of 1-heptene produced as a percentage of theoretical yield from 1-heptyne hydrogenated, in the same fashion as for FIG. 2 but at 20° C., with additions of excess $PMe_2Ph$. The addition of excess $PMe_2Ph$ was of molar equivalents of $PMe_2Ph$ of 5, 10 and 25 molar equivalents, a control also being shown where no excess was added. It was found that adding the excess $PMe_2Ph$ markedly increased the rate of 1-heptyne hydrogenation, and with increased additions the reaction rate approached the maximum hydrogen diffusion controlled rate obtainable under the experimental conditions in question. Other ligands such as $PPh_3$ were tested as stabilizing ligands, and gave similar results to those obtained when using excess $PMe_2Ph$. It is believed that in these cases the active catalyst cations probably contained a mixture of phosphine ligands. Similar results were obtained for other phosphine ligands in addition to $PMe_2Ph$ and $PPh_3$, with no detectable differences in catalyst selectivity, although reaction rates were generally lower than for the same amount of excess $PMe_2Ph$.

The re-usability of catalyst stabilized with excess $PMe_2Ph$ was tested, for the hydrogenation of 1-heptyne catalysed by $(RuH(PMe_2Ph)_5)^+$ at 20° C. and 1 atmosphere hydrogen pressure, the 1-heptyne being dissolved in methanol solvent and 25 molar equivalents of excess $PMe_2Ph$ being added. It was found that when the catalyst was used in a batch mode, deactivation still occurred. Thus, for example, sequential additions of 1-heptyne (equal batches of $1 \times 10^{-2}$ moles) added to a 50 ml catalyst solution showed that catalytic activity decreased by about 20% after the first addition and by a further 30% after a further four sequential batch additions. There was however no detectable effect on catalyst selectivity. The loss of catalyst activity observed in these tests is believed to be possibly a consequence of the mode of operation, and continuous operation, as opposed to batch operation, may give different results.

Figure 4:
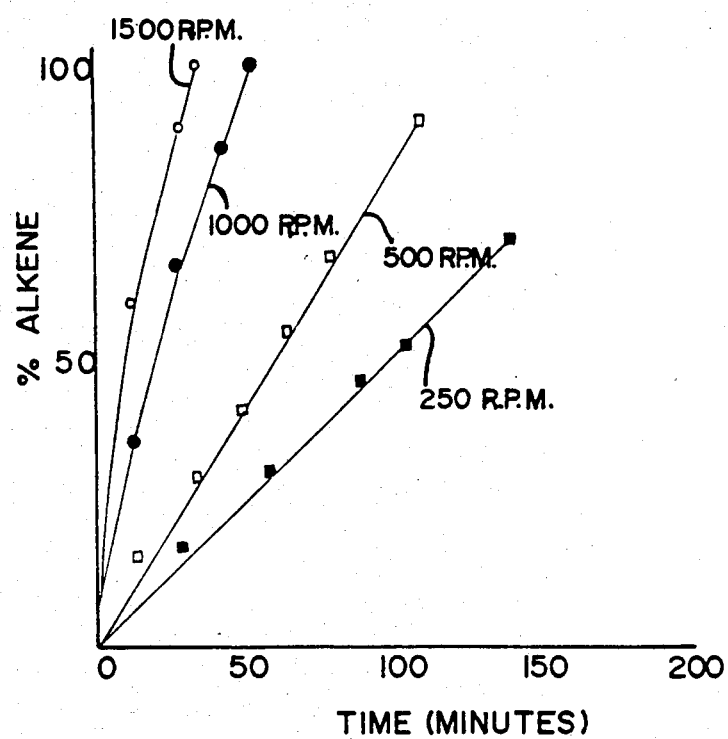
FIG. 4 is a plot against time of the proportion of alkene produced in a reaction mixture as a percentage of theoretical yield in still another process in accordance with the invention.

Finally, tests were conducted on the effect of stirring rate. In these tests, carried out according to the procedure described above, the alkyne was 1-heptyne dissolved in methanol containing 25 molar equivalents of excess $PMe_2Ph$, the catalyst cation being $(RuH(PMe_2Ph)_5)^+$ at 1 atmosphere hydrogen pressure at 20° C., but at different stirring rates of the magnetic stirring bar, namely 250, 500, 1000 and 1500 rpm. Results are shown in FIG. 4, which is a plot of alkene (1-heptene) produced as a percentage of theoretical yield against time, for the various stirring rates. It was found that with a high stirring rate of 1500 rpm, the hydrogenation of 1-heptyne occurred rapidly, taking about 40 minutes to completion. The catalytic hydrogenation of the 1-heptyne appeared to occur at hydrogen diffusion controlled rates, and it was noted that, even under high stirring rate conditions of 1500 rpm there was no detectable formation of heptane or isomerized heptenes.

Because of the high selectivity of alkyne hydrogenation to alkenes, the Applicant carried out an investigation on the selective hydrogenation of alkynes to alkenes, in the presence of alkenes. In a series of tests 1-hexyne ($1 \times 10^{-2}$ moles) made up to 50 ml in degassed methanol was selectively hydrogenated as described above to 1-hexene in the presence of equimolar amounts ($1 \times 10^{-2}$ moles) of 1-hexene, cyclohexene, 1,5-cyclooctadiene and 1,5-hexadiene. No detectable isomerization of the olefinic materials or formation of alkanes was found to take place. The hydrogenation of alkynes in relatively low concentrations relative to the corresponding alkenes was also investigated. Thus, hydrogenation of 1-hexyne in the presence of 1-hexene (molar ratio of 1-hexyne:1-hexene of 1:99) in methanol (as described above) occurred rapidly at 20° C. (under 10 minutes), once again with no detectable formation of hexane. Continuation of this hydrogenation for a further 20 hours gave no more than 0,06% detectable hexane formation, and no detectable hexene isomerization.

The aforegoing tests show that use of the complex six-coordinate ruthenium (II) cation $(RuH(PMe_2Ph)_5)^+$ derived from the complex $(RuH(PMe_2Ph)_5)_6$ precursor provides an extremely selective catalyst for the hydrogenation of alkynes to alkenes. The catalyst shows a negligible tendency to either isomerize or hydrogenate alkenes present or produced in the reaction mixture.

EXAMPLE 2

Further detailed tests were carried out to test the utility of the five-coordinate complex cation $(RuH (bis(diphenylphosphino)butane)_2)^+$ derived from the five-coordinate complex precursor $(RuH (bis(diphenylphosphino)butane)_2)PF_6$. The precursor complex was prepared and purified as described by Ashworth et al in *J. Chem. Soc., Chem. Commun.,* (1976) 705. Alkynes and alkenes to be hydrogenated were first purified by passage thereof through a short silica gel column, after which they were subjected to several freeze/thaw cycles under vacuum to remove air. Hexane and octane were used as non-interfering standards for gas/liquid chromatography analysis and were also de-oxygenated using freeze/thaw techniques.

A quantity of $1 \times 10^{-4}$ moles of said catalyst precursor was dissolved in nitrogen-degassed acetone, the total volume being made up to 50 ml, and were placed with a magnetic stirring bar in a 300 ml Schlenk flask.

The reaction solution was frozen at $-196°$ C. and the reaction flask evacuated to about $1 \times 10^{-1}$ torr. Hydrogen was charged into the flask at 1 atmosphere pressure and the reaction solution was warmed in a thermostat-controlled liquid (oil or water) bath to the reaction temperature, which was controlled to $\pm 0,1°$ C. Internal standard and alkyne were added by syringe in quantities respectively of $5 \times 10^{-3}$ moles and $1 \times 10^{-2}$ moles.

Progress of the reaction was monitored at 15 minute intervals by quantitative gas/liquid chromatography analysis using a Varian 3700 instrument with a 2,5 meter, 10% 1,2,3-tris(2-cyanoethoxy)propane on Chromosorb P-AW, column, the operating temperature for the monitoring being in the range 40°–60° C.

It was found that the five-coordinate complex cation in question readily hydrogenated 1-heptyne to 1-heptene and, more slowly, the 1-heptene produced heptane. This took place under the aforesaid mild reaction conditions at a temperature of 20° C. and a hydrogen pressure of 1 atmosphere. A reaction profile for the aforesaid reaction is shown in FIG. 5 which shows a plot of the proportion of 1-heptene present in the reaction mixture as a percentage of the theoretical yield, against time.

It appeared that the hydrogenation of the 1-heptyne to 1-heptene occurred at hydrogen diffusion controlled rates under the conditions in question. The quantity of 1-heptene in the reaction mixture subsequently dropped off because of the significantly slower subsequent hydrogenation of 1-heptene to heptane, and it appears that there was a moderate (typically greater than 99%) selectivity for alkyne hydrogenation over alkene hydrogenation. A further notable characteristic of the catalyst was that no alkene isomerization detectable by gas/liquid chromatography analysis occurred under the conditions in the catalysed reaction, 1-heptene being the only olefinic product observed during the hydrogenation of the 1-heptyne. The reaction profile shown in FIG. 5 is typical for most alkyne hydrogenation catalysts where selectivity is a function of two competing steps, namely alkyne hydrogenation and alkene hydrogenation respectively, but differs sharply from the profiles observed with regard to Example 1 above.

Figure 5:
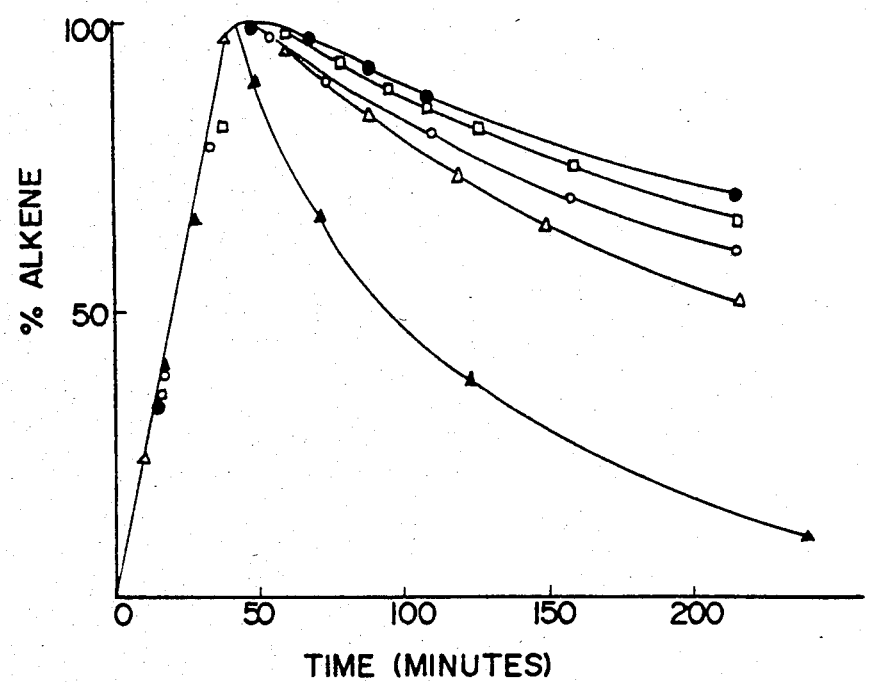
FIG. 5 is a plot against time of the proportion of alkene produced in a reaction mixture as a percentage of theoretical yield in a further process in accordance with the invention.

The hydrogenation of 1-heptyne employing the (RuH (bis(diphenylphosphino)butane)$_2$)$^+$ catalyst was further investigated employing solvent mixtures of acetone and methanol, whose reaction profiles are also shown in FIG. 5, the mixtures employed comprising acetone:methanol ratios on a volume basis of 4:1, 3:1, 1:1 and 1:3. The precursor was insufficiently soluble in methanol to permit a direct comparison using pure methanol as a solvent.

Employing the same apparatus and reaction conditions as before, it was found that the rate of 1-heptyne hydrogenation remained consistenly hydrogen diffusion controlled in all mixtures of the two solvents tested. However, the hydrogenation of 1-heptene, which occurred subsequent to 1-heptyne hydrogenation, was more sensitive to solvent changes, and this hydrogenation was found indeed to be markedly influenced by changes in solvent proportions. Thus, in methanol-rich solvent mixtures, olefin hydrogenation was more strongly favoured than in pure acetone. A direct consequence of this effect is that the selectivity of alkyne hydrogenation was slightly reduced and a selectivity of about 95% was observed in the 1:3 acetone/methanol solvent.

The aforegoing results suggest that the solvent may be used to control the selectivity of the alkyne hydrogenation reaction and further that the hydrogenation of alkenes is best carried out in a methanol-rich solvent mixture.

However, with regard to the reactions in methanol-rich solvent mixtures, it was observed that a precipitate was obtained comprising the neutral dihydride complex (RuH$_2$(bis(diphenylphosphino)butane)$_2$) which complex has been characterized by infrared spectroscopy and elemental analysis. No formation of this precipitate was observed in acetone solutions during the catalysed reactions, and it appeared that the rate of the formation of this precipitate paralled the methanol content of the solvent, the higher the methanol content the greater the amount of precipitate.

The formation of the aforegoing precipitate from (RuH(bis(diphenylphosphino)butane)$_2$) $^+$ and dihydrogen in alcohol solvents had been documented (Ashworth et al, *J. Chem. Soc., Chem. Commun.* (1976) 705). However, in keeping with the catalytic results, no evidence was found in the above tests for formation of this precipitate from the precursor and complex cation in question with dihydrogen in an acetone solvent, except in the presence of added base (Et$_3$N), when this precipitate was obtained in a quantitative yield. The precipitate was prepared from the aforesaid precursor in methanol, and was found to be sparingly soluble in acetone, and to show no catalytic activity in acetone or acetone/methanol solvent mixtures for either 1-heptyne or 1-heptene hydrogenation at 20° C. and a hydrogen pressure of 1 atmosphere. However, the addition of HBF$_4$ etherate in a quantity of $2 \times 10^{-4}$ moles to a suspension of the precipitate at a concentration of $2 \times 10^{-4}$ molar in these solvents rapidly generated a clear orange solution that hydrogenated both 1-heptyne and 1-heptene at 20° C. under hydrogen at 1 atmosphere pressure, in a manner closely analogous to that observed for the (RuH(bis(diphenylphosphino)butane)$_2$)$^+$ catalyst under identical conditions. These results appeared to show that the precipitate was not directly involved in the catalytic cycle in either acetone or acetone/methanol mixtures, and that the active catalyst cation could be generated from said neutral dihydride complex by treatment with acid. This dihydride complex can accordingly act as a precursor for the catalytic cations of the present invention.

Figure 6:
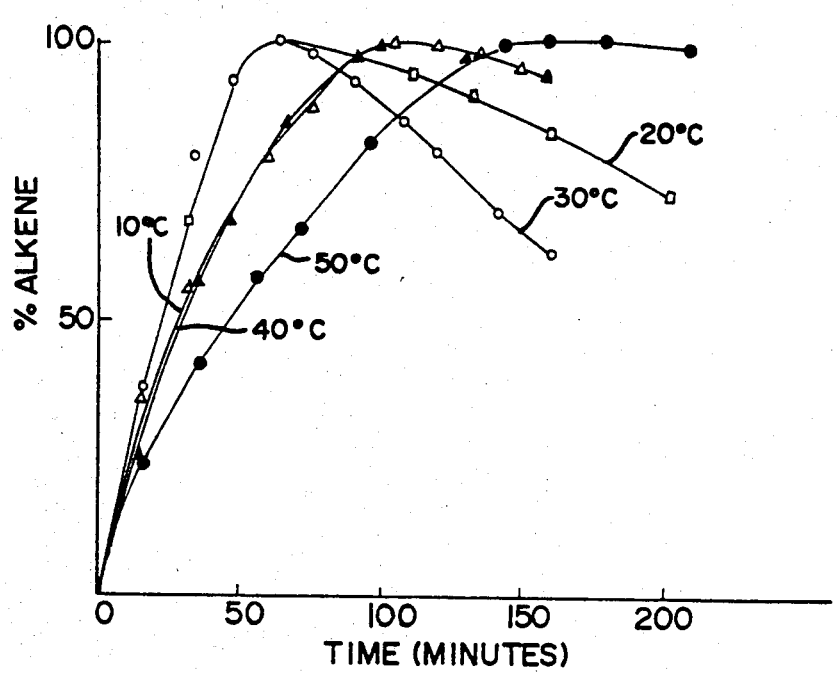
FIG. 6 is a plot against time of the proportion of alkene produced in a reaction mixture as a percentage of theoretical yield in a still further process in accordance with the invention.

Further investigations of the effect of temperature on 1-heptyne hydrogenation using the aforesaid complex cation catalyst derived from (RuH(bis(diphenylphosphino)butane)$_2$)PF$_6$ in acetone as solvent showed that the catalyst underwent irreversible deactivation at significant rates at temperatures in excess of about 30° C. Below 30° C., the expected dependence of the rate of hydrogenation on temperature was conformed to, as shown in FIG. 6 which is a plot of the 1-heptene produced as a percentage of theoretical yield against time at various temperatures respectively of 10°, 20°, 30°, 40° and 50° C. Above 30° C. there were found to be significant reductions in the rate of both 1-heptyne and 1-heptene hydrogenation, and stabilizing by addition of excess ligands to the solution was accordingly investigated.

Figure 7:
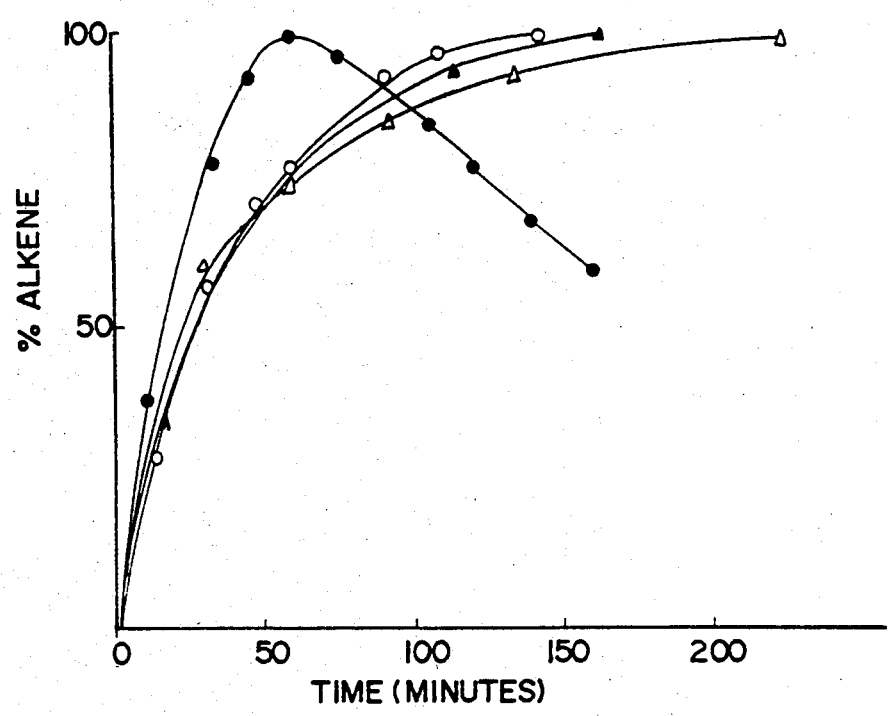
FIG. 7 is a plot against time of the proportion of alkene produced in a reaction mixture as a percentage of theoretical yield in yet a further process in accordance with the invention.

Excess bis(diphenylphosphino)butane ligand was accordingly added in subsequent tests, and showed that deactivation can be largely eliminated and reduced in this manner. Unexpectedly, it was also found that, in the presence of the excess phosphine ligand, the catalyst showed significantly enhanced selectivity for alkyne hydrogenation over alkene hydrogenation. Reaction profiles illustrating these effects are shown in FIG. 7 which is a plot of the proportion of alkene produced in the reaction mixture at a percentage of theoretical yield, against time, at 30° C. and 1 atmosphere pressure of hydrogen and in acetone solvent, for various additions of the phosphine ligand, namely in quantities of 1, 2,5, 5 and 10 molar equivalents.

The addition of 1 molar equivalent of phosphine ligand was found to slow the rate of 1-heptyne hydrogenation but, and more importantly, to eliminate the subsequent hydrogenation of 1-heptene. Analogous effects were also observed with increased amounts of ligand as shown in FIG. 7, but surprisingly these effects differed only slightly from the effects observed for 1 molar equivalent excess of the phosphine ligand.

Figure 8:
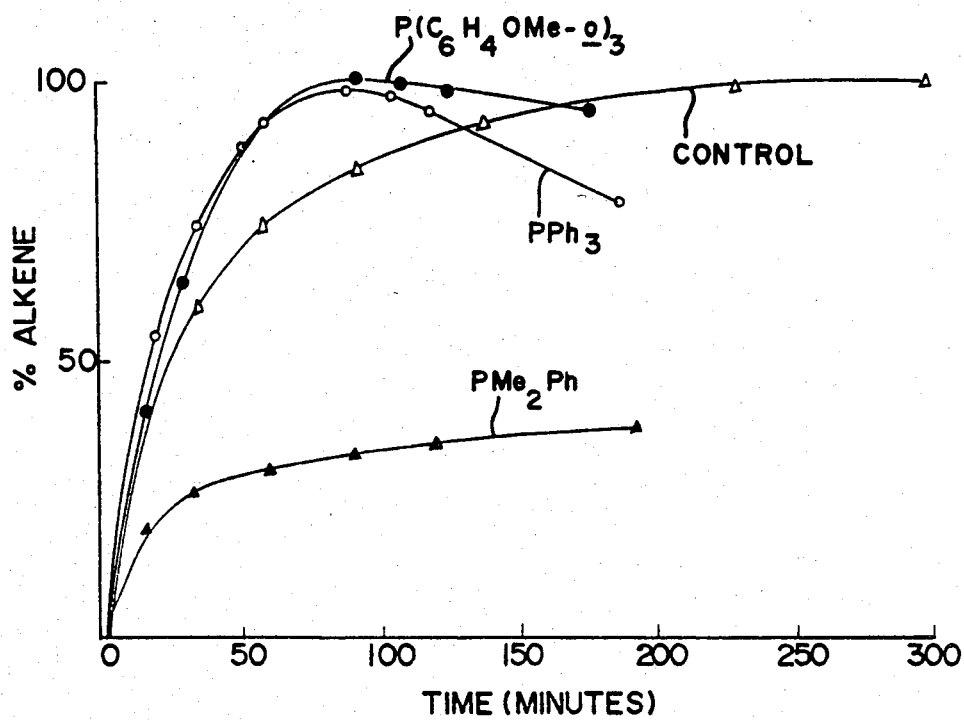
FIG. 8 is a plot against time of the proportion of alkene produced in a reaction mixture as a percentage of theoretical yield in an even further process in accordance with the invention.

Unidentate ligands were also found to be effective for increasing the selectivity of the catalyst and the reaction in question, as shown in FIG. 8, which is again a plot of the alkene present as formed in the reaction mixture, as a percentage of theoretical alkene yield, plotted against time. The tests were carried out at 30° C. under 1 atmosphere hydrogen pressure in acetone solvent, with addition in each case of 5 molar equivalents of various phosphine ligands, namely $PPh_3$, $P(C_6H_4OMe\text{-}o)_3$ and $PMe_2Ph$. As a control the test was also carried out with 2,5 molar equivalents of excess bis(diphenylphosphino)butane ligand. $P(C_6H_4OMe\text{-}o)_3$ gave a similar effect to the bis(diphenylphosphino)butane, while only minor effects were observed for $PPh_3$. In marked contrast, however, was the effect observed for $PMe_2Ph$. A significant deviation was found which corresponded closely to the results obtained in Example 1 hereinabove, under identical experimental conditions, and suggested that there was at least a partial or even complete substitution of the bidentate bis(diphenylphosphino)butane ligands in the complex catalyst ions by the more nucleophilic $PMe_2Ph$ monodentate ligands giving, very rapidly, a catalyst similar in character to that described in Example 1.

The above Examples demonstrate the aforegoing five-coordinate and six-coordinate ruthenium (II) complex cations and their precursors to be efficient homogeneous catalysts for the hydrogenation of both alkynes and alkenes. The catalysts show negligible tendencies, if any, to isomerize alkenes, and by suitable choice of solvents and stabilizing excess ligands, can be made selective, if necessary, for alkyne hydrogenation. Under stabilized conditions the catalysts can be made to show no material tendency to hydrogenate alkenes.

Further brief tests were conducted to test the catalyst of Example 1 as a supported, as opposed to a homogeneous, catalyst. These tests are described hereunder in Examples 3 and 4.

EXAMPLE 3

A catalyst precursor, namely $(RuH(PMe_3)_5)PF_6$ was supported on a celite (diatomaceous earth) particulate solid support, to test hydrogenation in the gas phase of alkynes. $5 \times 10^{-4}$ moles of the precursor together with $2,5 \times 10^{-3}$ moles of the stabilizing ligand $PPh_3$, and 1 gram of ethylene glycol were added to 3 grams of celite (100–200 ASTM mesh) together with 30 ml of methanol as solvent, to dissolve the catalyst components and to form a slurry with the celite. The methanol solvent was removed under vacuum with agitation of the slurry to ensure an even coating of the catalyst precursor, ethylene glycol and excess stabilizing ligand on the celite. The supported catalyst obtained in this fashion was a dry, free-flowing solid. The purpose of the ethylene glycol was to provide a light coating on the celite of a liquid which acts as a solvent for the catalyst cation and the stabilizing ligand on the surface of the celite catalyst support. This catalyst is thus of the type commonly known as a supported liquid phase catalyst.

A hydrogen stream containing 2% by volume of 1-heptyne was passed through a fixed bed of the supported catalyst, the bed having a diameter of about 1 cm and a height of between 6 and 8 cm, at a temperature of 25° C. and 1 atmosphere pressure for a period of 48 hours. Complete conversion of the 1-heptyne to 1-heptene was found to occur under these conditions and there was no detectable formation of isomers of 1-heptene under these conditions during the entire period of the test, and between 0,3 and 0,4% heptane formation.

Example 3 accordingly demonstrates the utility of the present invention for gas phase hydrogenation on a supported catalyst, in addition to the utility demonstrated by Examples 1 and 2 for liquid phase hydrogenation with the catalyst in homogeneous form.

EXAMPLE 4

A catalyst precursor similar to that of Example 1 and the same as that of Example 3, namely $(RuH(PMe_3)_5)PF_6$ was supported on a commercially available cation exchange resin to test the hydrogenation of alkynes in the solution phase but using a heterogeneous catalyst.

Commercial cation exchange resin (20,0 g, Amberlite IRC-50(H) in the carboxylic acid form) available from British Drug Houses (BDH) was thoroughly washed with methanol (2,0l) and dried. Catalyst precursor $(RuH(PMe_3)_5)PF_6$ (2,0g) in methanol solution (100 ml) was allowed to react with the resin for 48 hours at 25° C. under an atmosphere of nitrogen, the mixture being continuously stirred. At the end of this time the solvent was removed under vacuum and the resulting dry solid transferred to a Soxhlet extractor thimble. The solid was washed with methanol in a Soxhlet extractor for 16 hours under a nitrogen atmosphere to remove any unreacted $(RuH(PMe_3)_5)PF_6$. The washed resin was dried under vacuum and stored under nitrogen.

Resin supported catalyst (1.0 g) prepared in the above manner was added to a 200 ml Schlenk flask together with a magnetic stirring bar. Methanol (total volume made up to 20.0 ml) was added. The reaction mixture was frozen at $-196°$ C. and the reaction flask evacuated to about $1 \times 10^{-1}$ torr. Hydrogen was admitted to the flask at 1 atmosphere pressure and the reaction mixture warmed in a thermostat-controlled oil-bath to 40° C. ($\pm 0.1°$ C.). Internal standard (hexane $2,5 \times 10^{-3}$ mole) and heptyne ($5 \times 10^{-3}$ mole) were added by syringe.

The progress of the reaction was monitored at 15 minute intervals by quantitative gas/liquid chromatography analysis using a Varian Series 3700 instrument fitted with a 2,5 meter 10% 1,2,3-tris(2-cyanoethoxy)-propane on Chromosorb P-AW, column operating at 70° C. It was found that greater than 90% conversion of 1-heptyne to 1-heptene was achieved within 80 minutes with no concomitant formation of either isomerized heptenes or heptane. At this stage, for convenience, the reaction was left under these conditions for a further 20 hours (overnight). Complete consumption of 1-heptyne occurred with no detectable formation of either isomerized heptenes or heptane in the entire period. It is believed however that complete consumption of the 1-heptyne in fact occurred after about 120 minutes.

Example 4 demonstrates the utility of the invention when the catalyst is supported on a support and is heterogeneous.

EXAMPLE 5

The catalyst precursor $((C_8H_{12})RuH(NH_2NMe_2)_3)PF_6$ (in which $C_8H_{12}$ is cycloocta-1,5-diene and Me is methyl) when treated with tri-isopropylphosphite $(P(OPr^i)_3)$ in methanol, gives a catalyst precursor believed by the Applicant to be $(RuH(P(OPr^i)_3)_5PF_6$, i.e. $(RuXL_n)Y$ according to formula (2) in which X is H, L is P(OPr$^i$)$_3$, n is 5 and Y is PF$_6$. This methanol solution has been used to test the hydrogenation of acetylene (C$_2$H$_2$) in the solution phase.

An amount of ((C$_8$H$_{12}$)RuH(NH$_2$NMe$_2$)$_3$)PF$_6$(0.054 g, 1×10$^{-4}$ mole) was added to a Schlenk flask (400 ml capacity) together with a magnetic stirring bar. The flask was evacuated and filled with nitrogen gas. Methanol (25, 0 ml), previously purified by distillation under nitrogen, was added. Air-free tri-isopropylphosphite (2.0 ml) was added to the reaction mixture which was then frozen at −196° C. The reaction flask was evacuated to about 1.0×10$^{-1}$ torr. Hydrogen gas at 1.0 atomosphere was admitted to the flask and the reaction mixture was allowed to warm to 40° C. (±0.1° C.) using a thermostat-controlled water bath. The flask was then partially evacuated to give a hydrogen pressure of 0.82 atmosphere, and acetylene gas admitted to a final pressure of 1.0 atmosphere. The flask was immediately reconnected to a constant pressure (1.0 atmosphere) hydrogen source and the progress of the reaction monitored.

Sampling of the gas phase was carried out at 5–10 minute intervals, and the products monitored by gas/liquid chromatography using a Varian Series 3700 instrument fitted with a 2.0 m Porapak N column, available from Waters Associates, Inc., Maple Street, Milford, Mass., U.S.A., at greater than 99% conversion of acetylene to ethylene occurred within 40 minutes. Less than 0.5% ethane was formed during this time and over a further thirty minutes (70 minutes total reaction time), there was no detectable increase in the amount of ethane in the reaction mixture.

Example 5 accordingly demonstrates the utility of the present invention for the solution phase hydrogenation of acetylene and also demonstrates the in situ generation of the catalyst precursor, in this case believed to be RuH(P(OR$r^i$)$_3$)$_5$)PF$_6$, from the compound ((C$_8$H$_{12}$)RuH(NH$_2$NMe$_2$)$_3$)PF$_6$.

We claim:

1. A process for the hydrogenation of an unsaturated aliphatic hydrocarbon which comprises bringing an unsaturated aliphatic hydrocarbon to be hydrogenated into contact with hydrogen in the presence of a catalyst which comprises cations selected from the group consisting in five-coordinate and six-coordinate complex cations of ruthenium (II) having the general formula (1):

$$(RuXL_n)^+ \qquad (1)$$

in which
Ru is a ruthenium moiety;
X is a radical coordinated with the Ru;
L is a donor ligand; and
n is an integer not greater than 5.

2. A process as claimed in claim 1, in which the radical X is a radical selected from the group comprising H, Br, Cl, SO$_4$, NO$_3$, RSO$_3$ and RCOO in which R is H or a hydrocarbon radical.

3. A process as claimed in claim 1, in which at least one donor ligand L is a ligand selected from monodentate and bidentate ligands.

4. A process as claimed in claim 1, in which at least one donor ligand L is an organic molecule containing at least one atom selected from P, As, Sb and Bi.

5. A process as claimed in claim 4, in which at least one ligand L is a tertiary organic compound in accordance with the formula:

$$R^1R^2R^3E \qquad (3)$$

in which
E is an atom of P, As, Sb or Bi; and
R$^1$, R$^2$ and R$^3$ are the same or different radicals and are hydrogen, alkyl, aryl, aralkyl, alkaryl, substituted alkyl, substituted aryl, substituted aralkyl or substituted alkaryl, the substituents in R$^1$, R$^2$ and R$^3$ being selected from alkyl, aryl, aralkyl, alkaryl, aryloxy, alkoxy, hydroxy, halogeno, amino, amido and nitro groups.

6. A process as claimed in claim 4, in which at least one ligand L is a tertiary organic compound in accordance with the formula:

$$(R^1O)(R^2O)(R^3O)E \qquad (4)$$

in which
E is an atom of P, As, Sb or Bi; and
R$^1$, R$^2$ and R$^3$ are the same or different radicals and are hydrogen, alkyl, aryl, aralkyl, alkaryl, substituted alkyl, substituted aryl, substituted aralkyl or substituted alkaryl, the substituents in R$^1$, R$^2$ and R$^3$ being selected from alkyl, aryl, aralkyl, alkaryl, aryloxy, alkoxy, hydroxy, halogeno, amino, amido and nitro groups.

7. A process as claimed in claim 4, in which at least one ligand is a tertiary organic compound in accordance with the formula:

$$R^1R^2ER^3ER^4R^5 \qquad (5)$$

in which
E is an atom of P, As, Sb or Bi;
R$^1$, R$^2$, R$^4$ and R$^5$ are the same or different and are hydrogen, alkyl, aryl, aralkyl, alkaryl, substituted alkyl, substituted aralkyl or substituted alkaryl; and R$^3$ is substituted or unsubstituted alkyl, aryl, aralkyl or alkaryl, the substituents in R$^1$, R$^2$, R$^3$, R$^4$ and R$^5$ being selected from alkyl, aryl, aralkyl, alkaryl, aryloxy, alkoxy, hydroxy, halogeno, amino, amido and nitro groups, and R$^3$ being bonded to both of the E atoms.

8. A process as claimed in claim 4, in which at least one ligand L is a tertiary organic compound in accordance with the formula:

$$(R^1O)(R^2O)ER^3E(OR^4)(OR^5) \qquad (6)$$

in which
E is an atom of P, As, Sb or Bi;
R$^1$, R$^2$, R$^4$ and R$^5$ are the same or different and are hydrogen, alkyl, aryl, aralkyl, alkaryl, substituted alkyl; substituted aryl, substituted aralkyl or substituted alkaryl; and R$^3$ is substituted or unsubstituted alkyl, aryl, aralkyl or alkaryl, the substituents in R$^1$, R$^2$, R$^3$, R$^4$ and R$^5$ being selected from alkyl, aryl, aralkyl, alkaryl, aryloxy, alkoxy, hydroxy, halogeno, amino, amido and nitro groups, and R$^3$ being bonded to both of the E atoms.

9. A process as claimed in claim 4, in which at least one ligand L is selected from bis(diphenylphosphino)butane, bis(diphenylphosphino) propane, PMe$_3$, PMe$_2$Ph, P(OMe)$_2$Ph, PMe$_2$(C$_6$H$_4$OMe-o) and AsMe$_3$ in which Me is methyl and Ph is phenyl.

10. A process as claimed in claim 1, in which the unsaturated hydrocarbon to be hydrogenated is brought into contact with a stoichiometric excess of hydrogen.

11. A process as claimed in claim 1, in which the catalyst is homogeneous and the hydrogenation is carried out with the unsaturated hydrocarbon to be hydrogenated in the liquid phase, the catalyst being dissolved in the liquid phase and the hydrogen being in the gas phase.

12. A process as claimed in claim 11, in which said unsaturated hydrocarbon is dissolved in a solvent.

13. A process as claimed in claim 12, in which the solvent is a polar organic solvent.

14. A process as claimed in claim 13, in which the solvent is selected from alcohols, ethers and carbonyl compounds.

15. A process as claimed in claim 12, in which the liquid phase comprises, dissolved in the solvent, at least 0.1% on a molar basis of said unsaturated hydrocarbon.

16. A process as claimed in claim 11, in which the liquid phase comprises, dissolved therein, at least 0.1% on a molar basis of the catalyst.

17. A process as claimed in claim 1, in which the catalyst is heterogeneous and is supported on an inert support, a mixture containing said unsaturated hydrocarbon and hydrogen being passed over the supported catalyst.

18. A process as claimed in claim 17, in which said unsaturated hydrocarbon and the hydrogen are both in the gas phase.

19. A process as claimed in claim 1, in which said unsaturated hydrocarbon is an alkyne and is selectively hydrogenated to an alkene, the unsaturated hydrocarbon being brought into contact with the hydrogen in the presence of said catalyst and in the presence of excess ligands.

20. A process as claimed in claim 19, in which the excess ligands are selected from ligands in accordance with at least one of formulae (3), (4), (5), (6) and mixtures thereof.

21. A process as claimed in claim 19, in which the alkyne in the liquid phase and the excess ligands are dissolved in the liquid phase, the catalyst being homogeneous and being dissolved in the liquid phase, and the ratio on a molar basis between the excess ligands and the catalyst being between 1:1 and 100:1.

22. A process as claimed in claim 21, in which the ratio is between 15:1 and 20:1.

23. A process as claimed in claim 19, in which the catalyst is heterogeneous and is supported on an inert support, a mixture comprising said alkyne and hydrogen being passed over the supported catalyst, the mixture containing said excess ligands and the excess ligands being present in a proportion of at least 0.1% on a molar basis of the alkyne.

24. A process as claimed in claim 23, in which the mixture comprising said alkyne and hydrogen is in the gas phase.

25. A process as claimed in claim 19, in which the alkyne starting material which is hydrogenated forms part of a mixture comprising an alkene.

26. A process as claimed in any one of claims 19, in which the alkyne which is hydrogenated is acetylene and is hydrogenated to ethylene.

* * * * *

UNITED STATES PATENT AND TRADEMARK OFFICE
CERTIFICATE OF CORRECTION

PATENT NO. : 4,691,069
DATED : September 1, 1987
INVENTOR(S) : Michel O. ALBERS et al It is certified that error appears in the above-identified patent and that said Letters Patent is hereby corrected as shown below:

Column 11, line 39
    delete "the"
    change "catalyst" to -- catalysts--

Column 11, line 40
    before "of", insert -- similar to that --

Signed and Sealed this

Seventeenth Day of January, 1989

Attest:

DONALD J. QUIGG

*Attesting Officer*      *Commissioner of Patents and Trademarks*